US00PP19554P2

(12) United States Plant Patent
Zary

(10) Patent No.: US PP19,554 P2
(45) Date of Patent: Dec. 9, 2008

(54) HYBRID TEA ROSE PLANT NAMED 'JACTOROB'

(50) Latin Name: *Rosa hybrida*
Varietal Denomination: JACtorob

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,255

(22) Filed: Nov. 28, 2007

(51) Int. Cl.
*A01H 5/00* (2006.01)

(52) U.S. Cl. ..... Plt./137

(58) Field of Classification Search ..... Plt./137
See application file for complete search history.

*Primary Examiner*—Annette H Para
(74) *Attorney, Agent, or Firm*—Klarquist Sparkman, LLP

(57) ABSTRACT

Hybrid tea rose plant having flowers having a strong, tea rose fragrance, large blooms, hybrid tea bud and open flower form, vigorous, upright, well-branched plant, ease of propagation on its own roots, and near white petal reverse.

1 Drawing Sheet

Genus and species: *Rosa hybrida.*
Variety denomination: 'JACtorob'.

ORIGIN OF THE INVENTION

The present invention relates to a new and distinct variety of a hybrid tea rose plant named 'JACtorob' which was originated by me by crossing the variety 'KRIcarlo' (U.S. Plant Pat. No. 5,165, seed parent), with the variety 'JACsee' (U.S. Plant Pat. No. 11,138, pollen parent).

BACKGROUND OF THE INVENTION

The primary objective of this breeding was to produce a new hybrid tea rose variety having the upright, well-branched growth and hybrid form of the female (seed) parent combined with the fragrance and distinctive light petal reverse of the male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong, tea rose fragrance.
2. Large blooms.
3. Hybrid tea bud and open flower form.
4. Vigorous, upright, well-branched plant.
5. Ease of propagation on its own roots.
6. Near white petal reverse.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACtorob' differs from 'KRIcarlo' in flower color (coral for 'KRIcarlo' versus pink for 'JACtorob') and fragrance (little fragrance for 'KRIcarlo' versus strong fragrance for 'JACtorob'). 'JACtorob' differs from 'JACsee' in flower color ('JACtorob' is much more pink).

COMPARISON WITH SIMILAR VARIETY

The closest variety that the inventor is aware of is 'JACsee' (U.S. Plant Pat. No. 11,138). Besides flower color differences, 'JACtorob' has more petals than 'JACsee' (40 to 45 typical for 'JACtorob', 25–30 typical for 'JACsee', so ten more petals for 'JACtorob' is typical). 'JACtorob' is susceptible to powdery mildew in contrast to 'JACsee' which is resistant to powdery mildew.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—*'KRIcarlo' (U.S. Plant Pat. No.* 5,165).
*Pollen parent.*—'JACsee' (U.S. Plant Pat. No. 11,138).

FLOWER

Observations were made of plants of the new variety from January 2006 to November 2007 growing in a garden environment at Somis, Calif. The observations below are from plants that were four years of age at the end of the observation.

Blooming habit: Continuous.

Bud:

*Size*.—About 4–6 cm long and 3–4 cm in diameter when the petals start to unfurl.

*Form*.—The bud form is long, pointed ovoid.

*Color*.—When sepals first divide, bud color is White Group N155B tipped with Red Group 55B. When half blown, the upper sides of the petals are base color Red Group 56C with "handpainting" of Red Group 52B and the lower sides of the petals are White Group N155B tipped with Red Group 55B.

*Sepals*.—Color: Upper surface: Mainly Greyed-Green Group 191B. With Greyed-Purple Group 184B at base and Apex. Lower surface: Yellow-Green Group 146B. Length: 25 –30 mm. Width: 12–15 mm. Shape: Subulate. Surface: Upper: Hoary. Lower: Pubescent. There are three normally appendaged sepals. There are two unappendaged sepals with glandular and ciliolate edges.

*Receptacle*.—Color: Yellow-Green Group 144A. Shape: Apple. Size: Large, about 10 mm long×15 mm in width. Surface: Smooth.

*Peduncle*.—Length: Short, averaging about 3–5 cm. Surface: Prickly. Color: Yellow-Green Group 144A. Strength: Stiff, erect.

Bloom:

*Size*.—Large. Average open diameter is about 12 –14 cm.

*Borne*.—Singly.

*Stems*.—Strength: Normal. Average length is about 30–40 cm with a diameter of 4–6 mm.

*Form*.—When first open: High centered. Permanence: Becomes quill fashion.

*Petalage*.—Number of petals under normal conditions: 40–45.

*Color*.—The upper sides of the petals are Red Group 56C with "handpainting" of Red Group 52B. The reverse sides of the petals are White Group N155B tipped with Red Group 55B. The base of the petals has Green-Yellow Group 1B. The major color on the upper sides is Red Group 52B.

*Variegations*.—"Handpainting" of Red Group 52B as described above.

*Discoloration*.—The general tonality at the end of the first day: Red Group 56C with "handpainting" of Red Group 52B. At the end of the third day: Red Group 52B becomes Red Group 55A. Further aging: Changes to Red-Purple Group N66C by day 5.

*Fragrance*.—Strong, tea rose.

Petals:

*Thickness*.—Thick.

*Surface texture*.—Smooth.

*Shape*.—Obcordate.

*Margin*.—Entire.

*Apex shape*.—Obcordate.

*Base shape*.—Cuneate.

*Form*.—Moderately quilled.

*Arrangement*.—Imbricated.

*Petaloids*.—Number: 5–7. Color: Red Group 56C with handpainting of Red Group 52B.

*Persistence*.—Petals drop off cleanly before drying.

*Lastingness*.—On the plant: Long (about 7–8 days). As a cut flower: Long (about 8–9 days).

Reproductive parts:

*Stamens*.—Number: 75–85. Length: 11 mm. Anthers: Length: 3 mm. Color: Yellow-Orange Group 14D. Arrangement: Regular around styles. Filaments: Color: Yellow Group 9C. Length: 8 mm. Pollen: Color: Greyed-Orange Group 165C.

*Pistils*.—Number: 45–50. Length: 6–8 mm. Styles: Color: Greyed-Purple Group 186C. Length: 5–7 mm. Stigmas: Color: Yellow-White Group 158C. Length: 1 mm.

*Hips*.—None observed.

PLANT

*Form*.—Bush.

*Growth*.—Very vigorous, upright, branching.

*Age to maturity*.—Two years.

*Mature plant*.—Height: 180 cm. Width: 120 cm.

*Rootstock*.—Own root.

Foliage: Number of leaflets on normal mid-stem leaves: 5 or 7.

*Size*.—Medium. About 130 mm long×70 mm wide.

*Quantity*.—Normal.

*Color*.—New foliage: Upper side: Greyed-Red Group 178A, quickly turning to green. Lower side: Greyed-Red Group 178B, quickly turning to green. Old foliage: Upper side: Green Group 136A. Lower side: Yellow-Green Group 147B.

Leaflets:

*Size*.—About 35 mm long×25 mm wide.

*Shape*.—Oval.

*Base shape*.—Rounded.

*Apex shape*.—Acuminate.

*Texture*.—Leathery, smooth.

*Edge*.—Serrated.

*Serrations*.—Single.

*Petiole*.—Color: Lower Side: Yellow-Green Group 147B. Upper Side: Greyed-Purple Group183A.

*Petiole rachis*.—Color: Lower Side: Yellow-Green Group 147B. Upper Side: Greyed-Purple Group 183A. Underside: Rough with prickles.

*Auricles*.—Not observed.

*Stipules*.—Length: 20–23 mm, edged with numerous small glands.

*Disease resistance*.—Resistant to rust, susceptible to blackspot and mildew under normal growing conditions.

*Pest resistance*.—Nothing observed.

*Vein color*.—Yellow-Green Group 147B.

*Venation pattern*.—Reticulate.

Wood:

*New wood*.—Color: Yellow-Green Group 146C. Bark: Smooth.

*Old wood*.—Color: Yellow-Green Group 146A. Bark: Smooth.

Prickles:

*Quantity*.—Ordinary on main canes from base; 10–12 per 15 cm of cane. Ordinary on laterals from main canes; 10–12 per 15 cm of cane.

*Form*.—Hooked downward.

*Length*.—5–7 mm.

*Color when young*.—Greyed-Purple Group 183D.

*Color when mature*.—Greyed-Orange Group 166B.

Small Prickles:

*Quantity*.—On main stalks: None observed. On laterals: None observed.

Winter hardiness: Hardy to Zone 5.

I claim:

1. A new and distinct variety of hybrid tea rose plant, substantially as herein shown and described, characterized particularly by its strong, tea rose fragrance, large blooms, hybrid tea bud and open flower form, vigorous, upright, well-branched plant, ease of propagation on its own roots, and near white petal reverse.

* * * * *

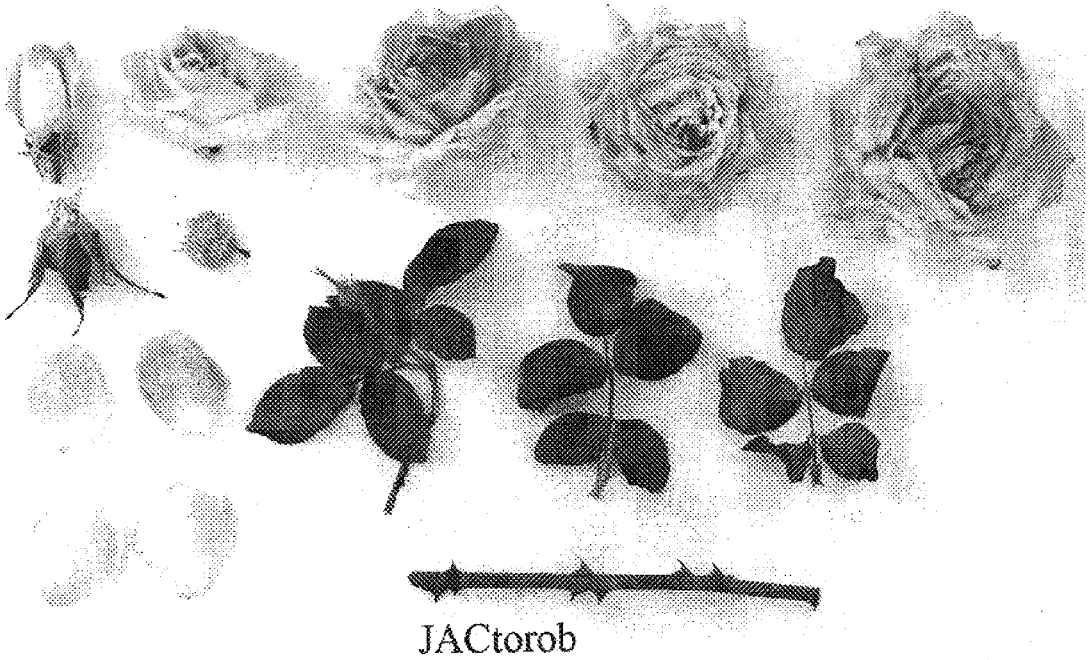
JACtorob